United States Patent
Morita et al.

(10) Patent No.: US 8,260,631 B2
(45) Date of Patent: Sep. 4, 2012

(54) VISUAL FILTERING TO CREATE LOGICAL ASSOCIATIONS IN TIMELINE BASED METAPHORS

(75) Inventors: Mark Morita, Arlington Heights, IL (US); Prakash Mahesh, Hoffman Estates, IL (US); Murali Kumaran Kariathungal, Hoffman Estates, IL (US)

(73) Assignee: General Electric Company, Schenectady, NY (US)

( * ) Notice: Subject to any disclaimer, the term of this patent is extended or adjusted under 35 U.S.C. 154(b) by 1125 days.

(21) Appl. No.: 11/595,317

(22) Filed: Nov. 10, 2006

(65) Prior Publication Data

US 2008/0114808 A1    May 15, 2008

(51) Int. Cl.
*G06Q 10/00* (2012.01)

(52) U.S. Cl. .......................................................... 705/2

(58) Field of Classification Search .................. 715/721, 715/781, 784, 785; 705/2, 3; 1/1; 707/10; 706/45
See application file for complete search history.

(56) References Cited

U.S. PATENT DOCUMENTS

| | | | |
|---|---|---|---|
| 5,493,677 A | | 2/1996 | Balogh et al. |
| 5,517,405 A | * | 5/1996 | McAndrew et al. ............ 706/45 |
| 5,982,369 A | | 11/1999 | Sciammarella et al. |
| 6,097,389 A | | 8/2000 | Morris et al. |
| 6,311,189 B1 | | 10/2001 | deVries et al. |
| 6,335,742 B1 | | 1/2002 | Takemoto |
| 6,396,963 B2 | | 5/2002 | Shaffer et al. |
| 6,408,301 B1 | | 6/2002 | Patton et al. |
| 6,486,896 B1 | | 11/2002 | Ubillos |
| 6,486,898 B1 | | 11/2002 | Martino et al. |
| 6,564,209 B1 | | 5/2003 | Dempski et al. |
| 6,567,980 B1 | | 5/2003 | Jain et al. |
| 6,784,925 B1 | | 8/2004 | Tomat et al. |
| 6,950,989 B2 | | 9/2005 | Rosenzweig et al. |
| 2003/0140044 A1 | * | 7/2003 | Mok et al. ........................ 707/10 |
| 2004/0243551 A1 | * | 12/2004 | Boone et al. ....................... 707/3 |
| 2007/0136296 A1 | * | 6/2007 | Molesky ........................... 707/10 |

* cited by examiner

*Primary Examiner* — Valerie Lubin (74) *Attorney, Agent, or Firm* — McAndrews, Held & Malloy, Ltd.; Armando Pastrana, Jr.

(57) ABSTRACT

Various embodiments of the presently described invention provide a method for visually representing associations among data and/or events presented on one or more timelines. A user is provided with the ability to select a filter that can be used to determine a plurality of data/events that are associated or related to one another according to the rule(s) defined by the filter. Once the associated data/events are determined, the association among the data/events is graphically presented to the user.

21 Claims, 4 Drawing Sheets

VISUAL FILTERING TO CREATE LOGICAL ASSOCIATIONS IN TIMELINE BASED METAPHORS

RELATED APPLICATIONS

Not applicable.

BACKGROUND OF THE INVENTION

The present invention generally relates to the search and analysis of electronic medical record ("EMR") data. More particularly, the present invention relates to methods and systems for visually representing associated data in one or more timelines.

Information and data can be visually presented to users in a variety of formats. For example, numerical and text data can be presented to users via a word processing application, a spreadsheet application or a web browser application, among others. In some instances, particular data is stamped, or recorded with, a time and/or date. For example, the time and/or date can represent when the data was collected or entered into a data storage system.

This time and/or date information can be used to present data in a chronological, or timeline fashion. This is an additional, useful manner in which data and information can be visually presented to a user.

However, as the amount of information or data presented to users in any of these and other formats increases, it becomes more and more difficult for users to understand and comprehend the information and the presentation of the information. For example, as more and more information is presented on a timeline, the timeline can become too cluttered for a user to obtain a useful understanding of the information presented in the timeline. In addition, it can become difficult for a user to quickly and easily see associations among the data.

This problem can occur in the presentation of medical data, for example. One manner in which medical data can be presented is in a timeline. However, this manner of presenting medical events can become confusing to users when a large number of medical events are presented. For example, a patient with multiple medical problems and frequent medical tests, imaging procedures and office visits, the presentation of medical events can be daunting. In addition, this presentation can be extremely difficult to determine which medical events and data represented on one or more timelines are related to one another and/or to a particular medical problem, caregiver/hospital encounter, medical procedure or hospital stay, for example.

Thus, a need exists for improving the methods in which events and data are presented to a user. The improved methods should present a visual association among related or associated events/data so that a user can quickly and easily see the associations among all related data and events.

BRIEF DESCRIPTION OF THE INVENTION

Various embodiments of the presently described invention provide a method for creating visual association among data. The method includes displaying one or more timelines that include one or more event symbols, where each of the event symbols representing an event, determining if a plurality of the event symbols represents a plurality of associated events, and visually representing an association among the associated events.

Various embodiments of the presently described invention provide a computer-readable storage medium comprising a set of instructions for a computer. The set of instructions including a display routine and a filter routine. The display routine is configured to display on a display device one or more timelines that include one or more event symbols, where each of the event symbols represents an event. The filter routine is configured to determine if a plurality of the event symbols represents a plurality of associated events, where the display routine is also configured to visually represent an association among the associated events on the display device.

Various embodiments of the presently described invention provide a method for visually representing associations among data. The method includes searching through medical data in an electronic medical record, determining if one or more associations exist among any of the medical data, and displaying at least a subset of the medical data in a chronological order and at least one geometric representation of the associations.

The foregoing summary, as well as the following detailed description of certain embodiments of the presently described technology, will be better understood when read in conjunction with the appended drawings. For the purpose of illustrating the invention, certain embodiments are shown in the drawings. It should be understood, however, that the present invention is not limited to the arrangements and instrumentality shown in the attached drawings.

DETAILED DESCRIPTION OF THE INVENTION

One or more embodiments of the presently described invention provide, among other things, an improved method for presenting data in such a way that associations among data and/or events are graphically presented to a user. In doing so, users can very easily and quickly see how data and/or events are related to one another. In addition, users can avoid being confused by visual clutter caused by unrelated data or events. One particular application of the presently described technology is in the presentation of medical events and data included in a patient's EMR in such a way that associations among events and data related to one another and/or to a particular medical problem, hospital visit, encounter or medical test/examination, for example.

Figure 2:
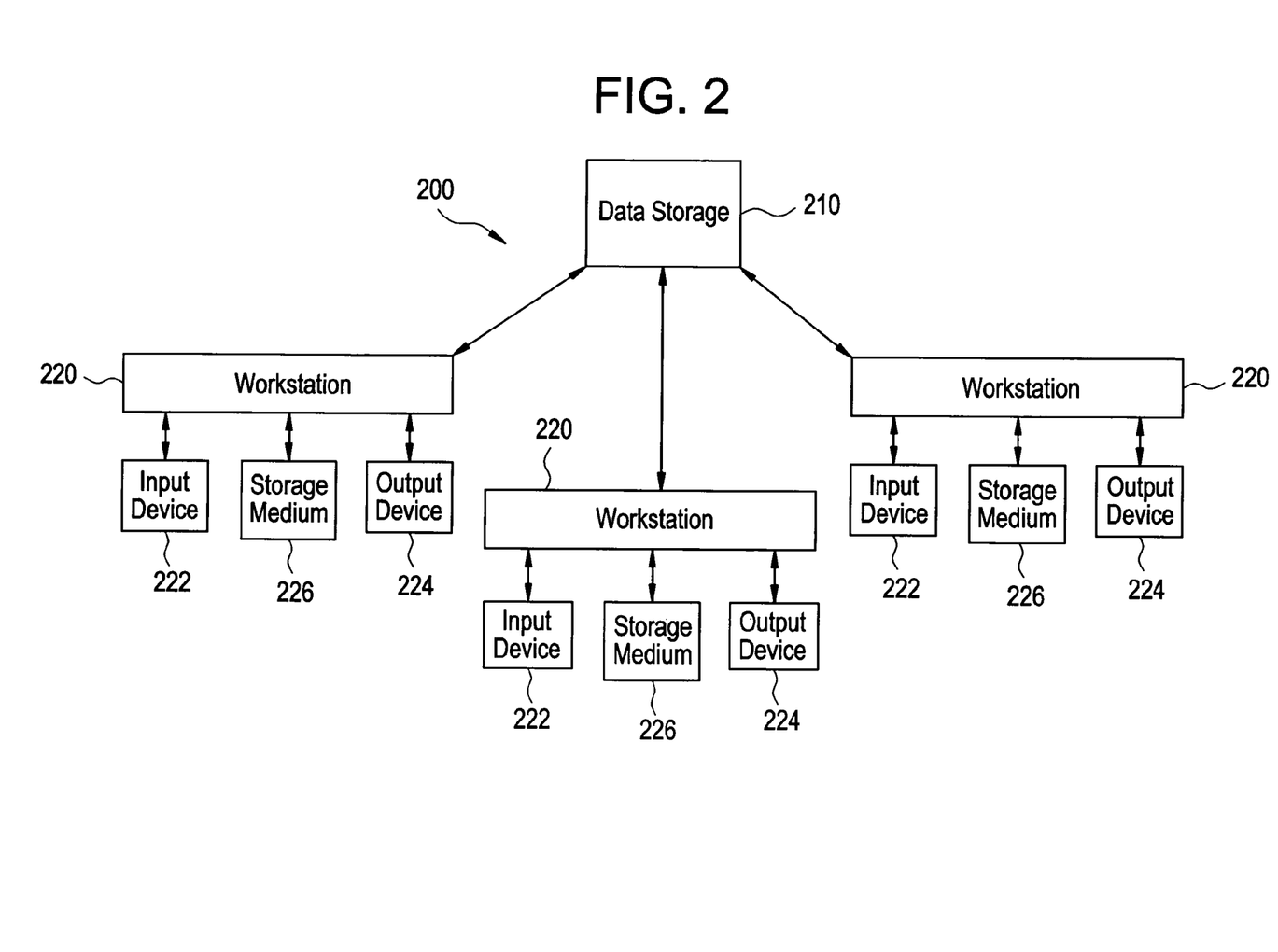
FIG. 2 illustrates a schematic diagram of a system for graphically presenting associations among related data and events in accordance with an embodiment of the presently described technology.

FIG. 2 illustrates a schematic diagram of a system 200 for graphically presenting associations among related data and events in accordance with an embodiment of the presently described technology. System 200 includes at least one data storage 210 and at least one workstation 220. While three workstations 220 are illustrated in system 200, a larger or smaller number of workstations 220 can be used in accordance with embodiments of the presently described technology. In addition, while one data storage 210 is illustrated in system 200, system 200 can include more than one data storage 210. For example, each of a plurality of entities (such as remote data storage facilities, hospitals or clinics) can each include one or more data stores 210 in communication with one or more workstations 220.

As illustrated in system 200, one or more workstations 220 can be in communication with at least one other workstation 220 and/or at least one data storage 210. Workstations 220 can be located in a single physical location or in a plurality of locations. Workstations 220 can be connected to and communicate via one or more networks.

Workstations 220 can be directly attached to one or more data stores 210 and/or communicate with data storage 210 via one or more networks. Each workstation 220 can be implemented using a specialized or general-purpose computer executing a computer program for carrying out the processes described herein. Workstations 220 can be personal computers or host attached terminals, for example. If workstations 220 are personal computers, the processing described herein can be shared by one or more data stores 210 and a workstation 220 by providing an applet to workstation 220, for example.

Workstations 220 include an input device 222, an output device 224 and a storage medium 226. For example, workstations 220 can include a mouse, stylus, microphone and/or keyboard as an input device. Workstations 220 can include a computer monitor, liquid crystal display ("LCD") screen, printer and/or speaker as an output device.

Storage medium 226 of workstations 220 is a computer-readable memory. For example, storage medium 226 can include a computer hard drive, a compact disc ("CD") drive, a USB thumb drive, or any other type of memory capable of storing one or more computer software applications. Storage medium 226 can be included in workstations 220 or physically remote from workstations 220. For example, storage medium 226 can be accessible by workstations 220 through a wired or wireless network connection.

Storage medium 226 includes a set of instructions for a computer (described in more detail below). The set of instructions includes one or more routines capable of being run or performed by workstations 220. The set of instructions can be embodied in one or more software applications or in computer code.

Data storage 210 can be implemented using a variety of devices for storing electronic information such as a file transfer protocol ("FTP") server, for example. Data storage 210 includes electronic data. For example, data storage 210 can store EMRs for a plurality of patients.

Communication between workstations 220, workstations 220 and data storage 210, and/or a plurality of data stores 210 can be via any one or more types of known networks including a local area network ("LAN"), a wide area network ("WAN"), an intranet, or a global network (for example, Internet). Any two of workstations 220 and data stores 210 can be coupled to one another through multiple networks (for example, intranet and Internet) so that not all components of system 200 are required to be coupled to one another through the same network.

Any workstations 220 and/or data stores 210 can be connected to a network or one another in a wired or wireless fashion. In an example embodiment, workstations 220 and data store 210 communicate via the Internet and each workstation 220 executes a user interface application to directly connect to data store 210. In another embodiment, workstation 220 can execute a web browser to contact data store 210. Alternatively, workstation 220 can be implemented using a device programmed primarily for accessing data store 210.

Data storage 210 can be implemented using a server operating in response to a computer program stored in a storage medium accessible by the server. Data storage 210 can operate as a network server (often referred to as a web server) to communicate with workstations 220. Data storage 210 can handle sending and receiving information to and from workstations 220 and can perform associated tasks. Data storage 210 can also include a firewall to prevent unauthorized access and enforce any limitations on authorized access. For instance, an administrator can have access to the entire system and have authority to modify portions of system 200 and a staff member can only have access to view a subset of the data stored at data store 210. In an example embodiment, the administrator has the ability to add new users, delete users and edit user privileges. The firewall can be implemented using conventional hardware and/or software.

Data store 210 can also operate as an application server. Data store 210 can execute one or more application programs to provide access to the data repository located on data store 210. Processing can be shared by data store 210 and workstations 220 by providing an application (for example, a java applet). Alternatively, data store 210 can include a stand-alone software application for performing a portion of the processing described herein. It is to be understood that separate servers may be used to implement the network server functions and the application server functions. Alternatively, the network server, firewall and the application server can be implemented by a single server executing computer programs to perform the requisite functions.

The storage device located at data storage 210 can be implemented using a variety of devices for storing electronic information such as an FTP server. It is understood that the storage device can be implemented using memory contained in data store 210 or it may be a separate physical device. The storage device can include a variety of information including a data warehouse containing data such as patient medical data, for example.

Data storage 210 can also operate as a database server and coordinate access to application data including data stored on the storage device. Data storage 210 can be physically stored as a single database with access restricted based on user characteristics or it can be physically stored in a variety of databases.

In an embodiment of the presently described technology, data storage 210 is configured to store data that is recorded with or associated with a time and/or date stamp. For example, a data entry can be stored in data storage 210 along with a time and/or date at which the data was entered or recorded initially or at data storage 210. The time/date information can be recorded along with the data as, for example, metadata. Alternatively, the time/date information can be recorded in the data in manner similar to the remainder of the data. In another alternative, the time/date information can be stored in a relational database or table and associated with the data via the database or table.

In an embodiment of the presently described technology, data storage 210 is configured to store medical data for a plurality of patients in a plurality of EMRs. The medical data can include data such as numbers and text. The medical data can also include information describing medical events. For example, the medical data/events can include a name of a medical test performed on a patient. The medical data/events can also include the result(s) of a medical test performed on a patient. For example, the actual numerical result of a medical test can be stored as a result of a medical test. In another example, the result of a medical test can include a finding or analysis by a caregiver that entered as text.

In another example, the medical data/events can include the name and/or results of an imaging procedure. Such imaging procedures include, but are not limited to, CT scans, MRI scans, photographs, tomographic images, and computer models, for example.

The medical data/events can also include a description of a medical visit. For example, the medical data/event can list the date and/or time of a visit to a hospital, doctor's office or clinic, as well as details about what tests, procedures or examinations were performed during the visit. In addition, the data/event can include results of the tests, procedures and examinations as described above. The data/event can include the names of all caregivers that came into contact or provided medical care to the patient during the visit. The data/event can also include information on the length of the visit, as well as any symptoms complained of by a patient and/or noted by a caregiver or other staff.

In another example, the medical data/events can include a description of a medical problem that a patient is experiencing. For example, an injury can be recorded as a medical problem, as well as any illnesses (chronic or otherwise) a patient is experiencing.

The medical data/events can also include details of a caregiver encounter. For example, the data/event can include information such as the date/time of an encounter with a doctor, nurse or other caregiver (such as a radiologist, for example). The data/event can include additional information such as what medical tests, examinations or procedures were performed on a patient by a specific caregiver. For example, if nurse "X" takes a blood sample from a patient, records the weight of a patient and tests the patient's blood pressure, then all of these tests and procedures, as well as the results, can be recorded as medical data/events associated with nurse X.

In another example, medical data/events can include a description and/or results of a medical procedure. For example, the name and outcome of a surgery or outpatient procedure can be recorded as a medical procedure.

Medical data/events can also include a description of any symptoms experienced by a patient. This information can be recorded as text or by a codification scheme. For example, medical data/events can include descriptions such as a headache, chest pains or dizziness.

The medical data/events stored in a patient's EMR can also include any biological analyses performed on the patient. For example, the data/events can include the numerical results of blood, enzyme or other fluid tests. In another example, the data/events can include a text description of the results of a biological analysis.

In another example, the medical data/events can include a finding by a caregiver. A finding can include any numeric and/or text-based description of a discovery or analysis made by the caregiver. For example, a radiologist can analyze a series of x-ray images of a patient and find a growth or tumor in the patient. The radiologist can then record his or her finding in a patient's EMR.

The medical data/events can also include one or more medications a patient is or has taken. The data can include the date, time, dosage and/or name of medication, for example.

The medical data/events can also include one or more data acquisitions. An acquisition can include any actual data acquired and/or the date at which the data is acquired. For example, an acquisition can include the results and/or date/time at which results from a laboratory test were acquired.

One or more types of similar data/events is included in a category of data/events. In continuing with the above example, a category of medical data/events can include all "tests" (including all test results or "test results" being a separate category), "imaging procedures" (including all images obtained therefrom or "images" being a separate category), "visit," "problems," "encounters," "medical procedures" (including all results or "medical procedure results" being a separate category), "symptoms," "biological analyses" (including all results of such analyses or "biological analysis result(s)" being a separate category), "findings," "medications," and/or "results."

While the above provides several examples of the types of medical data/events that can be used in accordance with embodiments of the presently described technology, it is to be understood that the presently described technology is not limited to the above data/events. In addition, while some types of information stored as medical data/events described above is repeated, it is to be understood that various medical data/events can be stored multiple times. For example, if a patient complains of a symptom to a caregiver during a particular office visit, the symptom can be recorded by itself and/or with additional information, such as the name of the caregiver and any procedures performed on the patient.

In an embodiment of the presently described technology, the medical data/events include the actual information desired to be stored. Alternatively, the medical data/events can include a code representative of the actual information desired to be stored. For example, the codes provided by the International Statistical Classification of Diseases and Related Health Problems ("ICD") can be stored in place of the actual information related to the medical data/event.

In operation, a user employs a workstation 220 to display, on an output device 224, at least a subset of data and/or events stored at data storage 210 in a chronological order with one or more associations among a plurality of the data and/or events visually represented to the user. As described above, workstation 220 includes computer-readable storage medium 226 that itself comprises a set of instructions for workstation 220. The set of instructions can be embodied in one or more computer software applications or computer code. This set of instructions is used by workstation 220 to access and display data and/or events and one or more associations among a plurality of the data/events. Thus, at least one technical effect of the set of instructions is to modify the display and presentation of at least a subset of data so as to enable a user to quickly and easily note associations among the data.

The set of instructions includes one or more software routines. In an embodiment of the presently described technology, the set of instructions includes a display routine, a data routine and a filter routine. These routines operate to determine and display associations among related data/events on display device 222, as described below.

Figure 3:
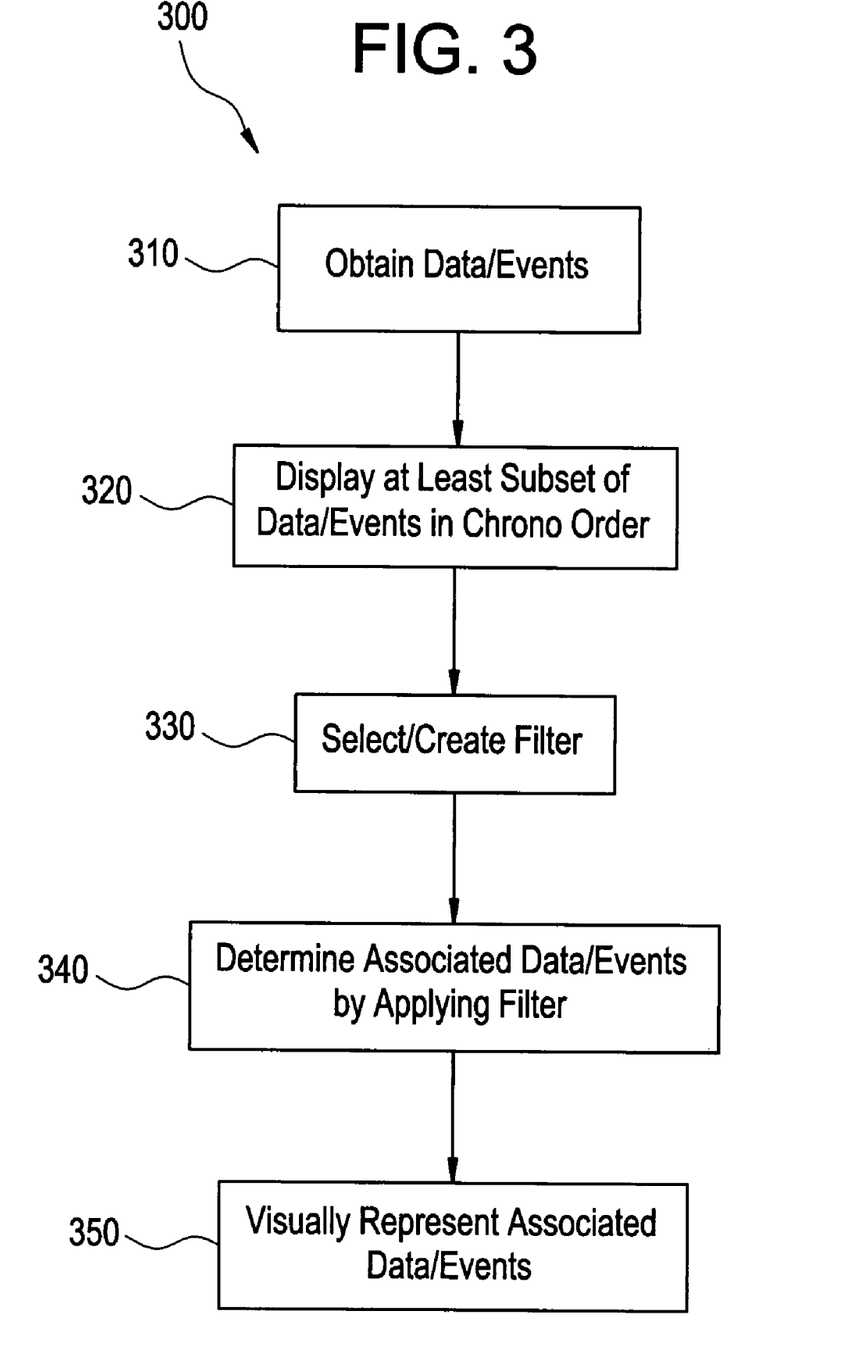
FIG. 3 illustrates a flowchart of a method for visually representing one or more associations among data and/or events in accordance with an embodiment of the presently described technology.

FIG. 3 illustrates a flowchart of a method 300 for visually representing one or more associations among data and/or events in accordance with an embodiment of the presently described technology. First, at step 310, data/events are obtained from data storage 210. The data routine of the set of instructions described above can obtain all or the data/events. For example, the data routine can copy or transfer all or a subset of medical data/events in a single patient's EMR from data storage 210 to workstation 220. In another example, medical data/events associated with a plurality of patients' EMRs is copied or transferred to workstation 220.

In an embodiment, all data included in a patient's EMR is transferred or copied from data storage 210 to storage medium 226 of workstation 220. In another embodiment, a user can limit the data transferred or copied by specifying limits on the data/events to be transferred or copied. For example, using input device 222, a user can select one or more of a date and/or time range or a category of medical data/events to be obtained from storage.

Figure 1:
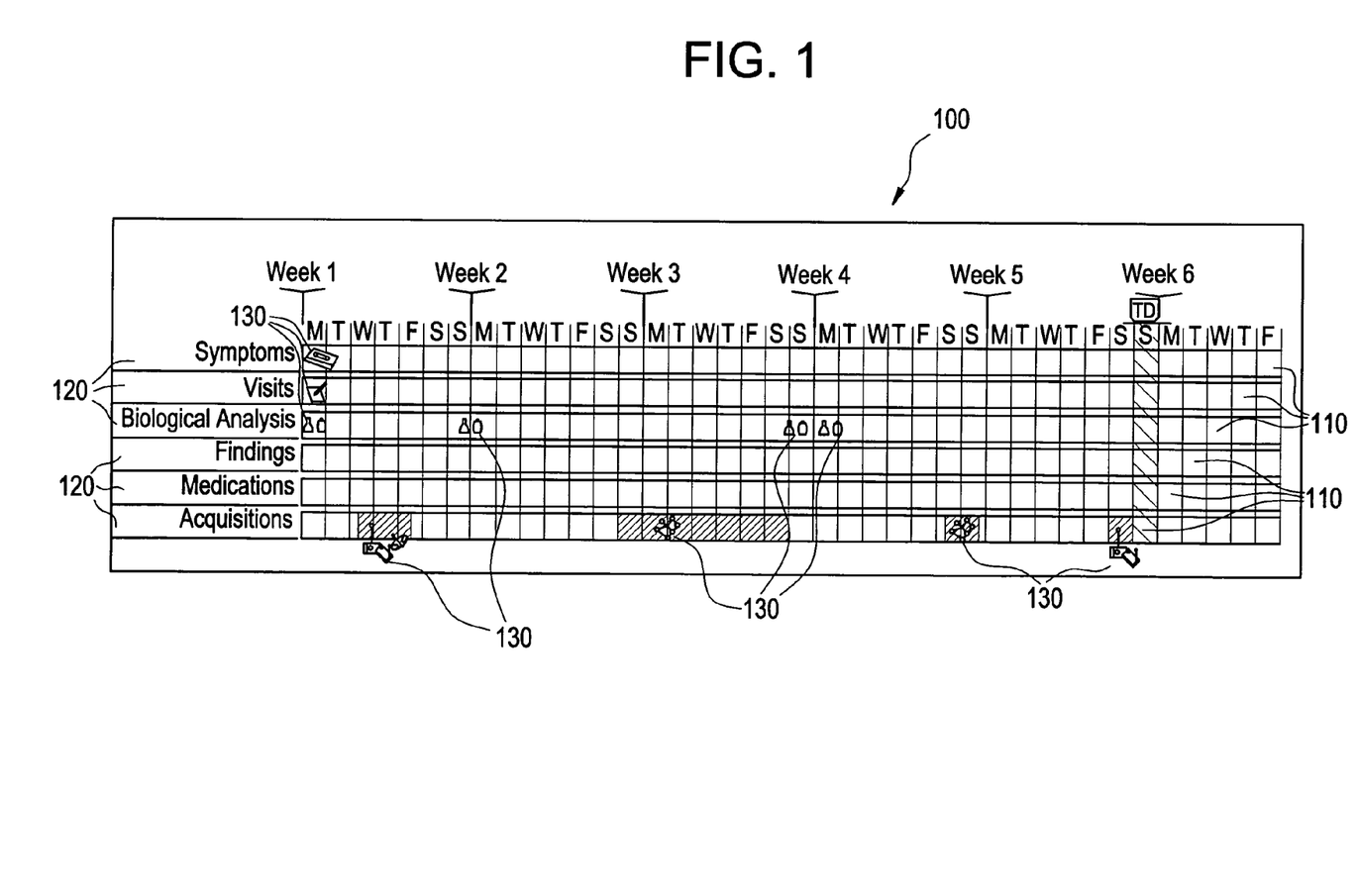
FIG. 1 illustrates a presentation of data/events in a plurality of timelines in accordance with an embodiment of the presently described technology.

Next, at step 320, at least a subset of the data/events obtained at step 310 is displayed on output device 224 at workstation 220. The data/events can be displayed by representing each of the data/events by a symbol on one or more timelines, for example. FIG. 1 illustrates a presentation 100 of data/events in a plurality of timelines 110 in accordance with an embodiment of the presently described technology. In presentation 100, several medical events are represented by symbols 130 in six different timelines 110. Each timeline 110 can include all medical events belonging to a particular category 120. These timelines 110 are also referred to as timeline metaphors. Timeline metaphors can be used in EMR software applications to provide users with the ability to navigate through a patient's medical history chronologically. In many cases, every patient encounter with a caregiver or hospital is listed as a separate item on a timeline 110. For example, presentation 100 can present medical events or data in timelines 110 illustrating the date and/or time at which the medical event or data occurred, was collected or was entered.

The display routine of the set of instructions can communicate with and cause output device 224 to display presentation 100, for example. Presentation 100 includes a plurality of timelines 110, a plurality of data/event categories 120 and a plurality of data/event symbols 130. While FIG. 1 illustrates a particular presentation 100, any part of it can be modified, increased in number or decreased in number without departing from the scope of the presently described technology.

In an embodiment of the presently described technology, each data/event is represented by a graphical symbol 130. The exact symbol used can differ in accordance with the presently described technology. In an embodiment, the same symbol is used for all similar data/events. For example, the same symbol can be used for all medical data/events in a category of data/events. In presentation 100 for example, the same symbol can be used for all data/events in timeline 110 which represents all data/events in the "symptoms" category 120.

A timeline 110 can include data/events from a given category 120 presented in chronological order. The number of timelines 110 therefore can change based on the number of categories 120 of data/events to be presented.

A user can select which categories 120 and/or timelines 110 are presented in presentation 100. For example, using input device 222, the user can select one or more categories 120 to be presented on output device 224. The display routine and the data routine can then obtain the data/events in the selected category(ies) 120 and display the data/events as shown in presentation 100 on output device 224. In addition, the user can select the date and/or time range over which the data/events are to be presented in timelines 110.

In an embodiment of the presently described technology, a user can scroll an icon over a symbol 130 and the display routine will cause additional information related to the symbol 130 to be presented to the user. For example, a user can employ input device 222 to move an arrow displayed on output device 224 over a symbol 130. Once the arrow is over the symbol 130 (or once the user "clicks" or otherwise selects the symbol 130 using input device 222), additional information about the data/event represented by symbol 130 can be presented by the display routine on output device 226. For example, the display routine can cause popup window to appear and present the actual data/event (or a portion thereof) represented by the symbol 130.

Next, at step 330, a filter is created by a user. The filter is used to determine which symbols 130 represent events/data that are associated with one another, if any.

The filter comprises one or more rules. These rules are compared to all or a subset of the events/data. If any of the events/data satisfy or match each of the rules, the events/data are considered to be associated with one another. Such events/data are referred to as associated events/data. If any of the events/data do not satisfy or match all of the rules, the events/data are considered to not be associated with one another.

In an embodiment of the presently described invention, a user creates a filter by employing input device 222 to select one or more predefined rules that are displayed on output device 226. The selected rules are then included in the filter.

In another embodiment, a user employs input device 222 to select a predefined filter. The predefined filter is a filter previously created by a user and stored on a computer-readable memory such as data store 210 or storage medium 226, for example.

The rules can include any criteria useful to determine whether a given data/event or subset of data/events fall within, or satisfy, the rule. For example, a rule can be stated as all data/events collected and/or entered during a particular patient's visit to a hospital. All data/events that were collected and/or entered during that visit would therefore fall within the scope of this rule and therefore be considered associated data/events.

In another example, a rule can define a set of data/events that are normally related with one another. For example, a typical doctor's office visit for a physical involves several routine tests such as tests on blood pressure, weight, reflexes, and/or blood. A rule can set a criteria that would include all medical data/events in a patient's EMR that includes information about and the results for blood pressure tests, weight measurements, reflex test results and blood test results. This rule can then be applied to a patient's EMR to determine which medical data/events includes data from blood pressure tests, weight measurements, reflex test results and blood test results. This data is then considered to be associated data.

In another example, a rule can define a criteria that associates all data/events related to a single patient encounter or a selected time and/or date range. Such a criteria can state that all data/events that were collected and/or entered during that encounter or during the time and/or date range selected by the user.

Another example of a rule is one in which all data/events from a particular medical test or examination are associated with one another. For example, a rule can state that all data/events describing a test and the results of that test are associated. Such a rule would associate a description of a blood test and all chemical and biological analyses from that blood test as associated data/events.

In another example, a rule can define a criteria that associates all data/events collected and/or entered by one caregiver or group of caregivers and excludes all data/events collected and/or entered by all other caregivers. For example, such a rule can associate all test results collected by a particular nurse and exclude all test results entered by other nurses.

In another example, a rule can define a criteria that associates all data/events with a predefined association with a selected medical problem and/or medical procedure. For example, the data/events stored at data store 210 can have a predefined association with one another based on an underlying problem or test. The medical problem of diabetes could have predefined association with tests such as eye examinations, foot examinations, blood sugar test results, hemoglobin A1c results and urine tests, for example. A medical procedure such as a surgery can have a predefined association with one or more caregivers' names involved in the surgery and in the recovery from surgery, test results related to the surgery and/or related symptoms, for example. All data/events with such predefined associations can be considered associated data/events according to such a rule.

The predefined associations can be stored or recorded in a variety of manners. For example, metadata included in the actual data/events stored at data store 210 can include the predefined associations. In another example, the actual data/events can have the predefined associations recorded in the data itself. A relational database or table stored at data store 210 can also include the predefined associations, for example.

Once the filter is selected or created by a user, method 300 proceeds to step 340 where the filter is used to determine if any associations exist among the data/events displayed on output device 226. The filter routine can determine if any associations exist among the displayed data/events by applying the filter selected or created at step 330 to the data/events. The filter routine can apply the filter by comparing the criteria defined by the rule(s) of the filter to the data/events displayed on output device 226. For example, the filter routine can apply the filter by searching through all or a subset of data/events stored at data store 210 and comparing the criteria of the filter rule(s) to the data/events.

In an embodiment of the presently described technology, the filter routine determines that data/events are associated data/events only if each and every one of the criteria defined by the filter is matched or satisfied. For example, if one criteria is not met by a particular data/event, then that data/entry is not considered to be associated with the data/events that meet each of the criteria.

In another embodiment of the presently described technology, the filter routine determines that data/events are associated data/events if a number of the criteria defined by the filter that is greater than a predefined threshold is matched or satisfied. For example, if a predefined threshold requires that 75% of the filter's criteria be met in order for the data/events to be associated data/events, any data/events that does not meet at least 75% of the criteria is not considered associated data/events. Conversely, all data/events that do meet at least 75% of the criteria are associated data/events, for example.

Once the associated data/events are determined, method 300 proceeds to step 350 where a visual representation of the associated data/events is created. In an embodiment of the presently described technology, the display routine causes a visual representation of the association among the associated data/events to appear on output device 226.

Figure 4:
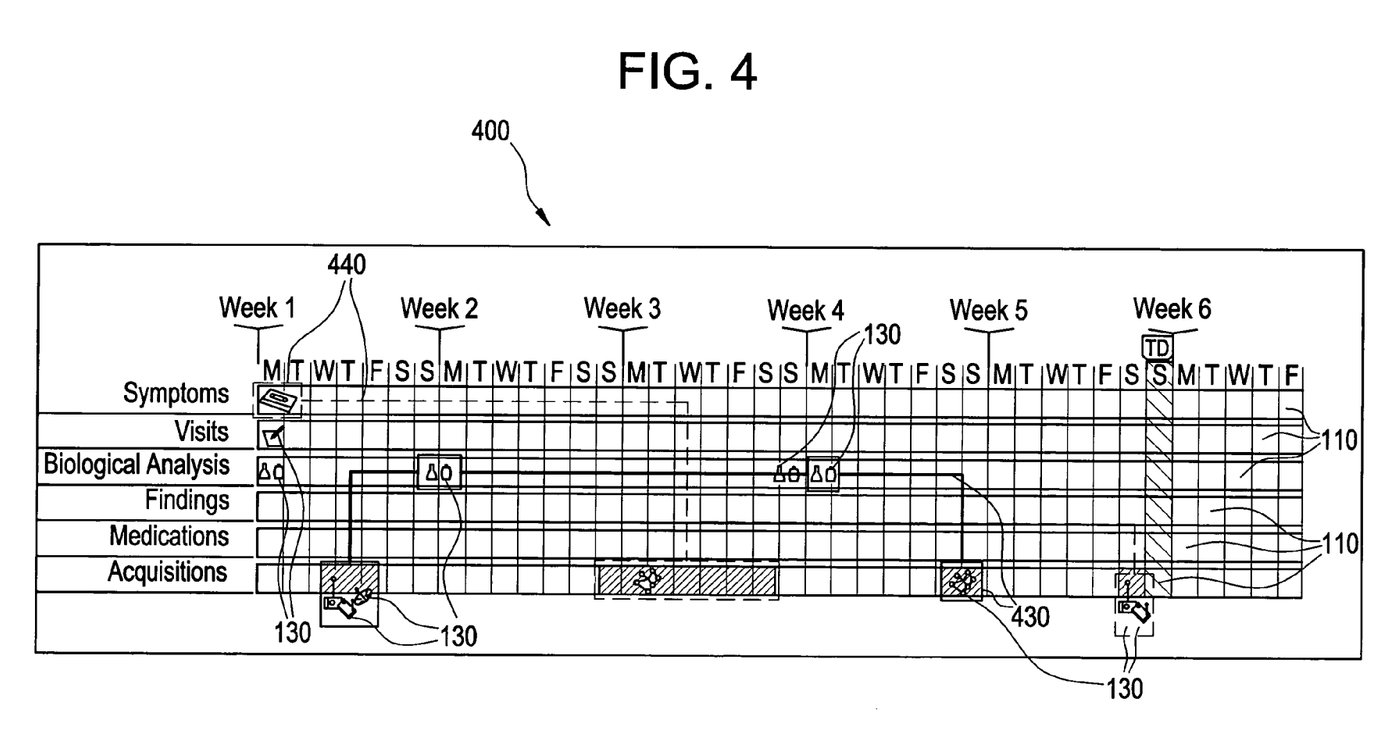
FIG. 4 illustrates a schematic of a presentation of data/event symbols on a plurality of timelines with a plurality of visual associations in accordance with an embodiment of the presently described technology.

FIG. 4 illustrates a schematic of a presentation 400 of data/event symbols 130 on a plurality of timelines 110 with a plurality of visual associations 430, 440 in accordance with an embodiment of the presently described technology. Presentation 400 is similar to presentation 100 with the addition of visual associations 430, 440 among associated data/events. As shown in FIG. 4, more than one association 430, 440 can be presented at a single time. In addition, one or more associations 430, 440 presented by display routine can exist between two or more data/events presented in different categories 120 or timelines 110. While FIG. 4 illustrates a particular presentation 400, any one or more components of presentation 400 can be modified, increased in number or decreased in number without departing from the scope of the presently described technology.

As described above, in an embodiment of the presently described technology, each data/event is represented by a graphical symbol 130. The exact symbol used can differ in accordance with the presently described technology. In an embodiment, the same symbol is used for all similar data/events. For example, the same symbol can be used for all medical data/events in a category of data/events. In presentation 400 for example, the same symbol can be used for all data/events in timeline 110 which represents all data/events in the "symptoms" category 120.

An association can be represented or displayed using any graphical object. For example, one or more lines can be displayed among symbols 130 of associated data/events. A line representing an association can cross one or more timelines 110 as one or more symbols 130 in each of a plurality of categories 120 can be associated with one another. In another example, one or more geometric shapes can surround one or more symbols 130 of associated data/events. Such geometric shapes can include a circle, oval, square, rectangle or triangle, for example. In addition, the geometric shape can surround one or more of symbols 130 of associated data/events. In another example, the association(s) among symbols 130 of associated data/events can be illustrated by changing the brightness, contrast and/or color of the symbols 130 representing a group of associated events/data. An association can also be represented by changing the symbol 130 used to represent associated events/data, for example.

In an embodiment of the presently described technology, one or more associations among symbols 130 of associated events/data can be displayed by the display routine causing only those symbols 130 of associated events/data to be displayed on output device 226 and by not displaying the symbols 130 of events/data that are not associated. That is, after an association is determined to exist between a plurality of events/data, only those symbols 130 representative of the associated events/data are displayed on output device 226 by the display routine.

In an alternative embodiment of the presently described technology, no symbols 130 representative of any data/events are displayed on output device 226 until after it is determined if any associations among the data/events exists. For example, step 320 can occur at or about the same time as step 350. That is, method 300 can proceed by first obtaining the data/events (step 310), then selecting/creating one or more filters (step 330), then determining whether a plurality of data/events are associated by applying one or more of the filters (step 340), then displaying the data/events (step 320) and any associations that exist among the data/events (step 350), for example.

One or more embodiments of the presently described invention provide several advantages. For example, embodiments of the presently described technology allow users to more clearly see relationships of data/events on a timeline due to graphical associations such as color coding and schematics that more clearly describe the relationships. In addition, embodiments of the presently described technology allow extraneous information to a particular data/event (such as a patient event, for example) to be disassociated with a particular grouping of associated data/events. In addition, using embodiments of the presently described technology, relevant information can be accessed without the uncertainty of accessing unrelated data/events that occur in close proximity to related data/events.

While one or more embodiments of the invention has been described with reference to example embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

In addition, while particular elements, embodiments and applications of the present invention have been shown and described, it is understood that the invention is not limited thereto since modifications may be made by those skilled in the art, particularly in light of the foregoing teaching. It is therefore contemplated by the appended claims to cover such modifications and incorporate those features that come within the spirit and scope of the invention.

What is claimed is:

1. A method for creating visual association among medical event data, said method including:
   using at least one computer processor to determine, for each of a plurality of medical events, a predefined association with a medical problem or a medical procedure, wherein each of the plurality of medical events corresponds to at least one of a date and time of occurrence for a patient, wherein the medical procedure is at least one of a medical test, a medical treatment, an imaging procedure and an operation;
   using the at least one computer processor to store the plurality of medical events to an electronic medical record of the patient in a data store, wherein the predefined association is stored in at least one of medical event data, medical event metadata and at least one table stored at the data store;
   using the at least one computer processor to retrieve information regarding the plurality of medical events from the data source;
   using the at least one computer processor and the retrieved information to determine that a first medical event is associated with a second medical event because both medical events include the predefined association with a same medical problem or a same medical procedure;
   using the at least one computer processor to present the associated first and second medical events in at least one timeline at a user interface operably connected to the at least one computer processor by:
      using a user interface to display a first symbol representative of the first medical event and a second symbol representative of the second medical event;
      using the user interface to display an indication of a chronological order of the first medical event and the second medical event; and
      using the user interface to visually associate the first symbol with the second symbol, thereby indicating that the first medical event is associated with the second medical event, the visual association being separate from the indication of the chronological order of the first medical event and the second medical event.

2. The method of claim 1, wherein the indication of the chronological order of the first medical event and the second medical event is a single timeline.

3. The method of claim 1, wherein the indication of the chronological order of the first medical event and the second medical event is a first timeline and a second timeline, the first medical event being displayed on the first timeline and the second medical event being displayed on the second timeline.

4. The method of claim 1, wherein each medical event comprises one or more of a medical test, a result of said medical test, an imaging procedure, a medical visit, a medical problem, a caregiver encounter, a medical procedure, a symptom, a biological analysis, a medical finding, a medication and an acquisition.

5. The method of claim 1, wherein the first and second medical events are determined to be associated because both medical events include the predefined association and both medical events occurred during a single patient encounter.

6. The method of claim 1, wherein the first and second medical events are determined to be associated because both medical events include the predefined association and both medical events occurred within a time range or date range.

7. The method of claim 1, wherein the first and second medical events are determined to be associated because both medical events include the predefined association and both medical events comprise a medical test or examination and one or more results of the test or examination.

8. The method of claim 1, wherein the first and second medical events are determined to be associated because both medical events include the predefined association and both medical events include data collected by a caregiver and exclude data collected by one or more other caregivers.

9. The method of claim 1, wherein the first and second medical events are determined to be associated because both events include the predefined association and both medical events satisfy a rule.

10. The method of claim 1, wherein the first and second medical events are determined to be associated because both medical events include the predefined association and both medical events satisfy a plurality of rules.

11. The method of claim 1, wherein the first and second medical events are determined to be associated because both events include the predefined association and both medical events satisfy a predefined threshold of a plurality of rules.

12. The method of claim 1, wherein the first symbol and the second symbol are visually associated by a line connecting the symbols.

13. The method of claim 1, wherein the first symbol and the second symbol are visually associated by a geometric shape that surrounds each symbol.

14. The method of claim 1, wherein the first symbol and the second symbol are visually associated by using a common color for the symbols.

15. A non-transitory computer-readable storage medium comprising a set of instructions for a computer, said set of instructions including:
   a first routine configured to determine, for each of a plurality of medical events, a predefined association with a medical problem or a medical procedure, wherein each of the plurality of medical events corresponds to at least one of a date and time of occurrence for a patient, wherein the medical procedure is at least one of a medical test, a medical treatment, an imaging procedure and an operation;
   a second routine configured to store the plurality of medical events to an electronic medical record of the patient in a data store, wherein the predefined association is stored in at least one of medical event data, medical event metadata and at least one table stored at the data store;
   a third routine configured to retrieve information regarding the plurality of medical events from the data source;
   a fourth routine configured to use the retrieved information to determine that a first medical event is associated with a second medical event because both medical events include the predefined association with a same medical problem or a same medical procedure;
   a fifth routine configured to use a user interface to display a first symbol representative of the first medical event and a second symbol representative of the second medical event;

a sixth routine configured to use the user interface to display an indication of a chronological order of the first medical event and the second medical event; and a seventh routine configured to use the user interface to visually associate the first symbol with the second symbol, thereby indicating that the first medical event is associated with the second medical event, the visual association being separate from the indication of the chronological order of the first medical event and the second medical event.

16. The medium and instructions of claim 15, wherein the indication of the chronological order of the first medical event and the second medical event is a single timeline.

17. The medium and instructions of claim 15, wherein the indication of the chronological order of the first medical event and the second medical event is a first timeline and a second timeline, the first medical event being displayed on the first timeline and the second medical event being displayed on the second timeline.

18. The medium and instruction of claim 15, wherein the first symbol and the second symbol are visually associated by a line connecting the symbols.

19. The medium and instruction of claim 15, wherein the first and second medical events are determined to be associated because both medical events include the predefined association and both medical events occurred during a single patient encounter.

20. The medium and instruction of claim 15, wherein the first and second medical events are determined to be associated because both medical events include the predefined association and both medical events occurred within a time range or date range.

21. The medium and instruction of claim 15, wherein the first and second medical events are determined to be associated because both medical events include the predefined association and both medical events comprise a medical test or examination and one or more results of the test or examination.

* * * * *